United States Patent [19]

Erb

[11] Patent Number: 4,798,452
[45] Date of Patent: Jan. 17, 1989

[54] AUTOCLAVABLE LASER BEAM MANIPULATOR

[76] Inventor: Robert C. Erb, 433 Brockmont Dr., Glendale, Calif. 91202

[21] Appl. No.: 784,379

[22] Filed: Oct. 4, 1985

[51] Int. Cl.⁴ .......................... A61B 17/36; A61B 1/06; G02B 7/18
[52] U.S. Cl. .......................... 350/632; 128/303.1; 128/395; 128/396; 350/639; 372/107
[58] Field of Search .......................... 350/631–635, 350/639; 372/107; 128/303.1, 395–398

[56] References Cited

U.S. PATENT DOCUMENTS

| 3,555,450 | 1/1971 | Rockwell, Jr. | 350/631 X |
| 3,642,353 | 2/1972 | Field | 350/634 |
| 3,670,263 | 6/1972 | Kantorski et al. | 372/107 |
| 3,866,140 | 2/1975 | Hobart et al. | 372/107 X |
| 3,887,270 | 6/1975 | Lazarus et al. | 350/634 X |
| 3,966,309 | 6/1976 | Mohler | 350/633 |
| 3,986,854 | 10/1976 | Scrivo et al. | 128/397 X |
| 4,064,466 | 12/1977 | Seki et al. | 372/107 |
| 4,211,229 | 7/1980 | Wurster | 128/303.1 |
| 4,278,324 | 7/1981 | Zipfel | 350/633 |
| 4,479,225 | 10/1984 | Mohler et al. | 350/631 X |
| 4,575,853 | 3/1986 | Jako | 372/107 X |
| 4,597,380 | 7/1986 | Raif et al. | 128/395 X |

Primary Examiner—John Petrakes
Attorney, Agent, or Firm—Frank L. Zugelter

[57] ABSTRACT

An autoclavable laser beam manipulator, made of non-corrosive materials forming its elements which in turn contribute to a novel construction for this instrument that is used with endoscopes of all kinds. Aircraft grade aluminum forms elements such as housing and piston. Laser grade uncoated molybdenum forms the mirrored element mounted on the piston and disposed within a chamber for the housing. Glass-filled DELRON material forms a member which contributes to the adjustment of location and position of the mirrored element to change the direction of laser beam egress from the device, thus controlling such direction.

11 Claims, 2 Drawing Sheets

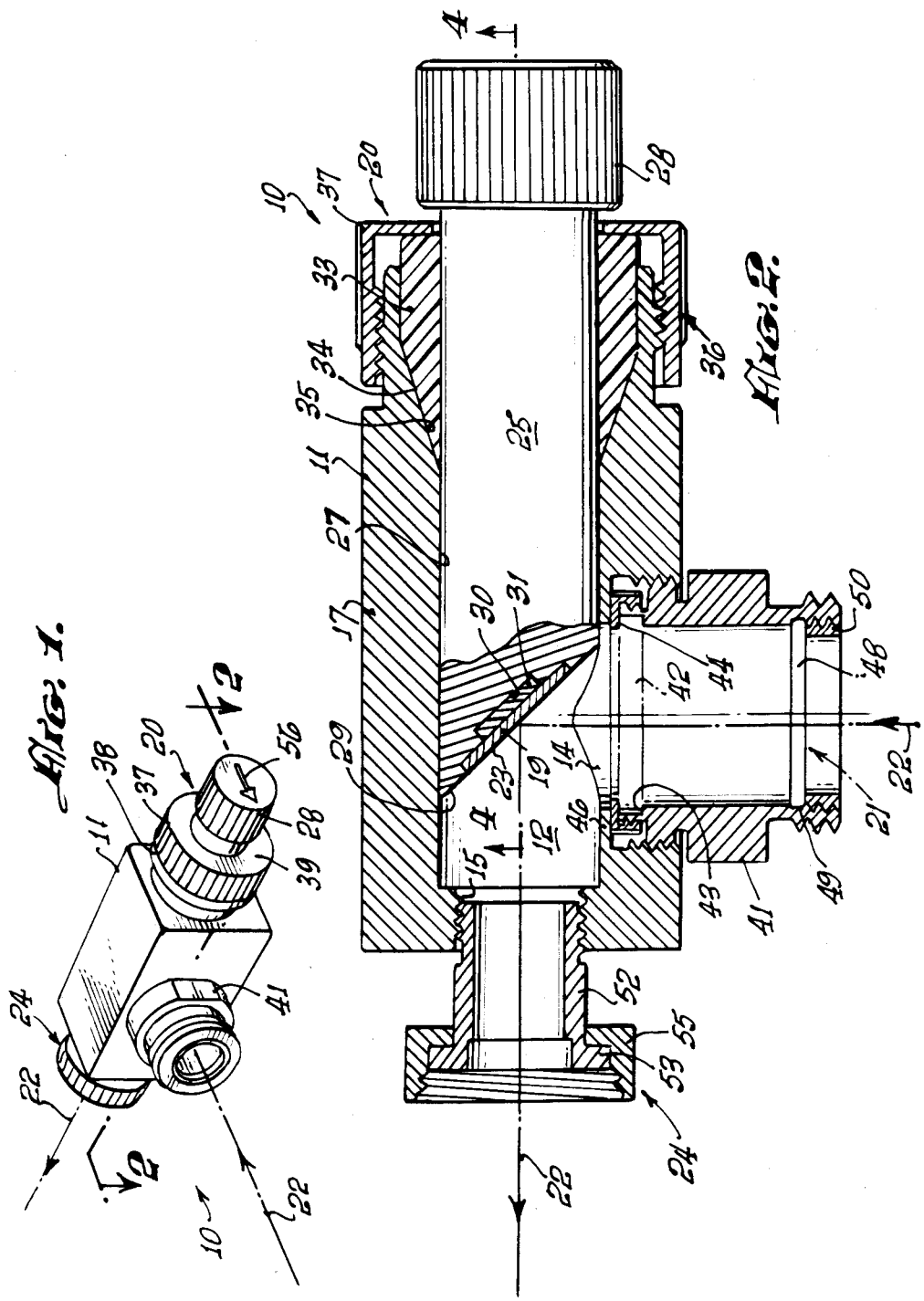

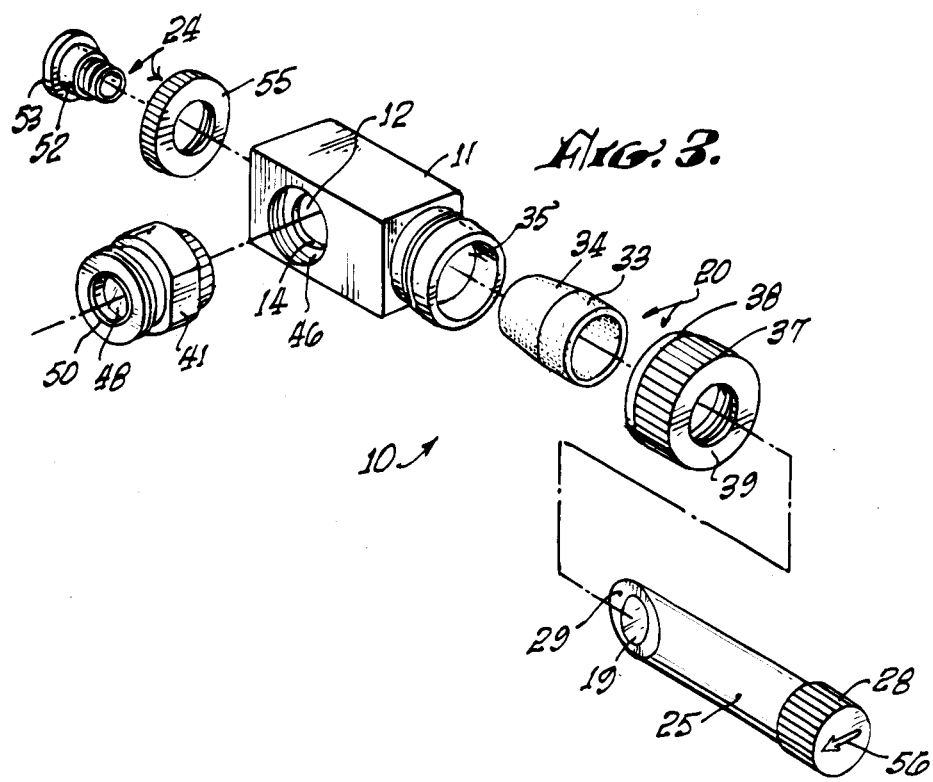
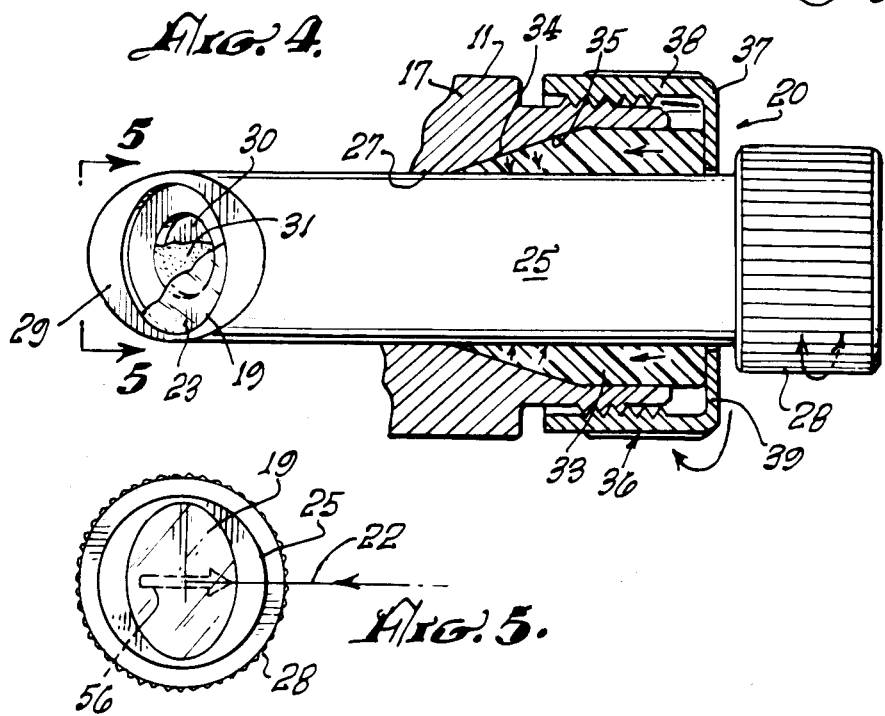
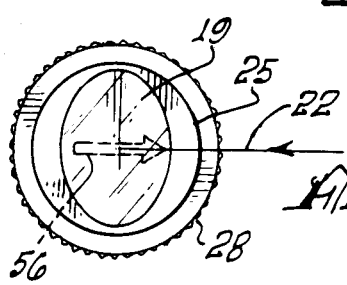

AUTOCLAVABLE LASER BEAM MANIPULATOR

TECHNICAL FIELD

This invention relates to surgical devices which manipulate laser beams to tissue target areas for their treatment during surgical procedures, and in particular to sterilization of the manipulators and a novel construction therefor.

BACKGROUND

In surgical procedures, the surgeon's hands and instruments held my him, such as scapels and other bacteria-carrying implements, and which contact or are to contact the patient's body, particularly in an exposed body area undergoing treatment, are sterilized so that such hands and instruments and the like that do touch the patient's area being surgically treated are not contaminated with foreign bacteria harmful to the patient. By sterilizing these instruments then, they are not contaminated in a way harmful to the patient and of course, the are useful to the surgeon in successfully treating the patient.

Heretofore, no laser beam manipulator used in surgical operations was capable of being sterilized, because of its materials not being able to stand the stress or strain of autoclaving conditions. The materials would corrode, and in particular, would pit were they autoclaved. Consequently, the precise gimballing movements or motion, which are required in changing the direction of and controlling the treating laser beam, would be detrimentally affected were sterilization of the unit attempted. These manipulator assemblies were surgically cleaned by other methods which would remove contaminating bacteria. This invention produces a unique instrument by reason of its ability to be sterilized, thereby eliminating corrosion of its component parts and by the novel construction incorporating the materials discovered for its parts to make the laser beam manipulator autoclavable. Also, the construction itself, irregardless of nature of materials, is novel.

Further, the materials forming some elements of the invention include the characteristic of non-warping, i.e., not getting out of shape, because of the conditions accompanying the autoclavability of the manipulator. Thus, precise movement for these elements is maintained after autoclaving, and which provides the desired kind and degree of control of the laser beam. These elements include housing, gimballing elements (the piston here) and the compressible member in the adjusting means, and the mirrored element.

DISCLOSURE OF THE INVENTION

This invention comprises a process by which a laser beam manipulator is autoclavable, thus, non-contaminated, namely, by forming such instrument with a set of parts formed from materials that do not corrode under autoclaving conditions; a product formed by such process; and an instrument incorporating a unique construction of elements to effect a desired control for directing a laser beam to its target area during a surgical procedure being carried out.

The mirror, by which the beam is reflected and by its changed position and location in the manipulator controls the direction of the reflected beam, is formed from an uncoated laser grade molybdenum. An aircraft grade aluminum material is utilized for the gimballing system elements and housing of the manipulator, and a 20% glass-filled DELRON material is utilized in one of the elements forming an adjusting means in operating the manipulator. The glass-filled characterisitc of the DELRON material is provided for withstanding stresses that develop on the element during autoclaving of the device.

The gimballing system of the illustrated embodiment comprises, in addition to the materials of its elements, a mirrored element mounted on a body that is both rotatable and linearly displaceable, the body being in a chamber of a housing having ingress and egress ports for corresponding transmissions of a laser beam into the chamber and then from the chamber after being reflected off of the mirrored element. The body is actuatable from exteriorly of the housing, by the grasping fingers of the surgeon or operator of the instrument, while adjusting means to simultaneously restrict and change its universal motion is provided. The body itself, along with the mirrored element secured thereto, includes materials that are non-corrosive, such as the examples set out above, and which are not susceptible to the effects of conditions associated with an autoclaving method or vessel. The selection of these materials extends to the housing, the adjusting means, and other components of the device. Facile detachment for a focusing lens assembly adapted to be connected to a laser beam source is provided at the ingress port for the housing, and a detachable adapter assembly by which the device is suitably mounted to a surgical instrument housing is provided. With these latter two assemblies being detached, the remainder of the manipulator is autoclavable.

An object of this invention is to provide an autoclavable laser beam manipulator.

Another object of this invention is to provide a method of sterilizing a laser beam manipulator without corroding its elements.

A further object of this invention is to provide a novel laser beam manipulator to thereby provide for its autoclavability.

A still further object of this invention is to use an autoclave vessel for sterilizing a laser beam manipulator.

These and other objects and advantages will become more apparent upon a full and complete reading of this disclosure comprising this description, the appended claims thereto, and the accompanying drawing comprising two (2) sheets of five (5) FIGURES.

BRIEF DESCRIPTION OF THE DRAWING

FIG. 1 is a perspective view of an embodiment of the invention.

FIG. 2 is a view taken on line 2—2 of FIG. 1.

FIG. 3 is an exploded perspective of the view of FIG. 1.

FIG. 4 is a view taken on line 4—4 of FIG. 2.

FIG. 5 is a view taken on line 5—5 of FIG. 4.

BEST MODE OF CARRYING OUT THE INVENTION

Referring now to the drawing FIGS. 1-5 wherein reference characters refer to like numerals hereinafter, reference character 10, FIG. 1, identifies the illustrated embodiment of the invention. Laser beam manipulator 10 comprises a housing 11 having a chamber 12 with which ingress and egress ports 14, 15, respectively, communicate therewith, a gimballing system body 17 which extends into chamber 12 and having mounted thereon in an inclined fashion a mirrored element 19 in general alignment with both ingress and egress ports 14, 15, and an adjusting assembly 20 of elements for body 17 and by which the latter's rotating and lineal displacements are adjusted and controlled in the operation of the manipulator 10. A lens assembly 21 for focusing a laser beam 22 prior to its incidence upon a face 23 of mirrored element 19 is suitably detachably mounted to body formation in housing 11 for ingress port 14, while an adaptor assembly 24 is suitably detachably mounted to body formation in housing 11 for egress port 15.

In more particularity, gimballing system body 17, formed of aircraft grade aluminum comprises a cylindrical configuration 25, such as a piston, slip fit to a bore 27 formed in housing 11, also of aircraft grade aluminum material, and in communication with chamber 12, and in this embodiment in alignment with egress port 15. A finger-grasping member 28 is integrally formed proximate the one terminus for piston 25, it being disposed exteriorly of housing 11 for actuation of piston 25, while mirrored element 19, formed from a laser grade uncoated molybdenum, is mounted to piston 25 at its other terminus disposed within chamber 12, upon an inclined face 29 of piston 25 so that laser beam 22 entering ingress port 14 strikes upon and reflects therefrom and out of egress port 15.

Two recesses are provided in inclined face 29 of piston 25, the first (not referenced) for deposit of the mirrored element 19 whereby the latter's mirrored face or plane 23 is flush with face 29, while the second recess 30, FIG. 2, is provided behind that first recess for depositing an epoxy 31 therein to secure element 19 in its recess to piston 25. Epoxy 31 is of a nature which in curing bonds the nature of mirrored element 19 to the nature of body 17 forming the cylindrical configuration of piston 25.

Adjusting assembly 20 comprises a sleeve 33 (made from the noted DELRON material) mounted in slip-fit fashion about configuration 25, sleeve 33 including an annular taper 34 that complements a conical wall 35 forming an opening, communicable with chamber 12, in housing 11 into which sleeve 33 inserts, and a compressing member 36, such as an open-top cap 37. Cap 37 conventionally threads by its circular wall 38 to housing 11, as seen in FIG. 2, and its open top is formed by an annular flange 39 integrally formed upon circular wall 38. Flange 39 provides an even distribution of pressure against sleeve 33 when adjusting its tightness or looseness within conical wall 35. Sleeve 33 extends beyond housing 11 so that flange 39 compresses or wedges sleeve 33 to a desired degree in the operation of manipulator 10.

Lens assembly 21 comprises a collar 41 suitably threaded to corresponding threaded body formation forming ingress port 14, with one lens 42 seated on a shoulder 43 provided in collar 41, retained on shoulder 43 by a threaded open-top cap member 44 the top of which in turn seats on an apertured base 46 forming ingress port 14, while another lens 48 is mounted in collar 41 on a shoulder 49 located proximate its outer terminus, being secured thereto by a threaded retainer washer 50. Assembly 21 may take any construction and form of materials desired and required for a manipulator 10, as it is detachable from housing 10 prior to exposure or introduction of the device to the step of autoclaving.

Adaptor assembly 24 comprises a collar 52 having its one end correspondingly threaded to body formation in housing 11 forming egress port 15. A terminal flange 53 is integrally formed at its other end and to which a threaded retainer ring 55 is mounted and by which manipulator 10 is operatively connected to a housing for a surgical instrument (not shown). Assembly 24, being detachable, is constructed of suitable materials known and in use for surgical instruments of the type involved, and like lens assembly 21, need not be assembled to device 10 for the purpose of autoclaving it. An arrow 56 is mounted atop member 28, and is correlated to the plane of mirror face 23, such as by being perpendicular thereto, to inform the user or surgeon of the disposition of such face 23 during operation of the instrument.

In operation with reference to a surgical procedure, a laser beam 22 is introduced into chamber 12 through the lens of assembly 21 mounted at ingress port 14, to strike mirror face 23 and reflect therefrom through chamber 12 and through egress port 15, continuing its transmission to, say, a tissue target area being treated by the laser beam. To change direction of the reflection beam discharging through egress port 15, cap member 37 is manually loosened so that pressure is released from the wedging action of sleeve 33 against conical wall 35, thereby making cylindrical configuration or piston 25 lineally and/or rotatably displaceable. The release is not one which makes configuration 25 freely moveable in its bore 27. Rather, a frictional engagement between the walls forming bore 27 and configuration 25 continues, so that a conscience or deliberate finger tactile sense upon finger member 28 is required to cause such displacement or motion. In this manner, mirrored face 23 is moved in universal or three-dimensional (or less) direction to effect the degree of change of direction of laser beam 22 desired. Upon achieving such change of direction, cap member 37 is rotated in a tightening fashion upon sleeve 33 to again compress or wedge same against conical wall 35, as contrasted to a mere frictional engagement between these two elements. Such tightening assures the exact desired positioning of configuration 25 and thus mirrored face 23. Also, no contamination occurs.

Assembly of manipulator 10 is provided by taking the fabricated elements of manipulator 10, shown in FIG. 3, and joining them together as shown and suggested in FIG. 4. Annular taper 34 of sleeve 33 is inserted into the opening provided by conical wall 35, and thereafter, cap 37 is mounted to its projecting portion and threaded loosely to housing 11. The inclined face 29 of configuration 25 is introduced into chamber 12 through open-top cap 37 and sleeve 33, after which the former is tighten down, compressing or wedging sleeve 33, and to thereby adequately stationarily position configuration 25 until device 10 is ready for surgical use. Each of the assemblies 21, 24 is previously assembled as shown and suggested in FIG. 2, after which they are attachably mounted to their respective body formations forming ingress and egress ports 14, 15.

The autoclaving step of the invention embraces a number of sterilization techniques known today, as well as any that may develop, to put into a sterile condition the materials in laser beam manipulators. By present day standards, such manipulators can be sterilized in a conventional autoclave vessel utilizing in known manner steam temperature and pressure. A gaseous suspension within a vessel, such as ethylene oxide, also is capable of sterilizing these manipulators. Another form of autoclaving is soaking them in a cold liquid such as the product CIDEX, made and sold by Johnson and Johnson Company, 1 Johnson and Johnson Plaza, New Brunswick, N.J. 08933. A flash (using light) technique, is another known technique to sterilize articles.

The above described elements of manipulator 10 are fabricated by known manufacturing processes and techniques as applied to machining, milling, molding and other conventional operations to form such elements.

Epoxy 31 is of a suitable and known nature for bonding molybdenum and aluminum together. Other means, such as a screw arrangement, can be used to secure the mirrored element to the piston. Other suitable assembles 21, 24 also can be mounted in known manner to housing 11, and such assembles also may be formed of non-corrosive and non-warping materials so that they, one or both, may be autoclaved if desired.

Industrial Applicability

The invention is utilized in the surgical medical field.

SUMMARY

In summary, herein disclosed is an autoclavable laser beam manipulator that is used with all kinds of endoscopes, the manipulator being sterilized for use with such surgical instruments, and wherein its gimballing system controls the location and position of the laser beam by actuation thereof. The autoclavability of the manipulator is not limited in its form to that illustrated, so long as it includes non-corrosive materials forming its elements or of the particular materials of such elements as disclosed herein. Too, the construction of the manipulator itself is deemed unique. And no only non-corrosive materials are used, but also the nature of the material for autoclavability includes a non-warping (getting out of shape, i.e.) characteristic so that precise movements of the elements changing the direction of the laser beam is maintained.

Various changes and modifications may be made without departing from the spirit and scope of the invention. Lens assembly 21 can be suitably detachably mounted about egress port 15 as well as at its present location. The invention is not limited to the above illustrated embodiment or its application to such illustrated embodiment.

I claim:

1. An autoclavable laser beam manipulator comprising an aircraft grade aluminum housing having a chamber and ingress and egress ports,
   an aircraft grade aluminum gimballing system mounted to and in the chamber of said housing,
   a laser grade uncoated molybdenum mirrored element secured to said gimballing system within the housing's chamber, and
   a glass-filled plastic member forming an adjusting means for said mirrored element.

2. The manipulator of claim 1 wherein said plastic member is 20% glass-filled.

3. The manipulator of claim 1 or claim 2 including
   a lens assembly for focusing a laser beam on the mirrored element, and
   an adaptor assembly for mounting said manipulator to a laser beam source.

4. A laser beam manipulator comprising
   a housing having a body,
   body formations in said housing forming light ingress and egress ports, said ports angularly inclined to one another, said body formations for such ports adapted to mount lens and laser beam source assemblies,
   said housing including a chamber communicating with said ports,
   a piston reciprocably and rotatably mounted in the chamber and extending outwardly of said housing,
   a mirrored element mounted on and in inclined fashion to said piston and disposed in the chamber so that light right through the ingress port reflects therefrom through the egress port, and
   means mounted about said piston for adjusting its reciprocating and rotating displacements,
   whereby change of location and position for said mirrored element is effected and thereby change direction of the reflected light through the egress port.

5. The manipulator of claim 4 wherein said adjusting means comprises a wedging assembly.

6. The manipulator of claim 5 where in said body includes a bore, an annular taper thereto, and said wedging member comprises
   a tapering sleeve complementing said annular taper and an adjustable retainer means mounted about said sleeve and operatively connected to the housing for compressing said sleeve upon said piston and against the annular taper.

7. The manipulator of claim 6 wherein said adjustable retainer means comprises a threaded cap with an open top threaded to the housing.

8. A laser beam manipulator having a housing with a bore therein and ingress and egress ports for a laser beam said housing having a body having a chamber connected to such ports, and characterized by a reciprocatable and rotatable piston mounted in said bore, said piston having a mirrored element mounted thereon and disposed in the chamber in an inclined fashion to each of such ports, and means mounted about the piston for adjusting its reciprocating and rotating displacements.

9. The manipulator of claim 8 wherein said adjusting means comprises a wedging assembly.

10. The manipulator of claim 9 wherein said body includes an annular taper about said bore and said wedging assembly comprises
    a tapering sleeve complementing said annular taper and an adjustable retainer means mounted about said sleeve and operatively connected to the housing for compressing said sleeve upon said piston and against the annular taper.

11. The manipulator of claim 10 wherein
    said adjustable retainer means comprises a threaded cap with an open top threaded to the housing.

* * * * *